(12) United States Patent
Possover

(10) Patent No.: US 11,931,565 B2
(45) Date of Patent: Mar. 19, 2024

(54) SURGICAL APPLICATION TOOL FOR IMPLANTATION OF AN ELECTRODE WIRE

(71) Applicant: Marc Possover, Hagendorn (CH)

(72) Inventor: Marc Possover, Hagendorn (CH)

(*) Notice: Subject to any disclaimer, the term of this patent is extended or adjusted under 35 U.S.C. 154(b) by 199 days.

(21) Appl. No.: 17/221,973

(22) Filed: Apr. 5, 2021

(65) Prior Publication Data

US 2021/0353935 A1    Nov. 18, 2021

(30) Foreign Application Priority Data

Apr. 7, 2020   (DE) .................. 10 2020 109 730.1

(51) Int. Cl.
    *A61N 1/05*       (2006.01)
    *A61B 17/00*     (2006.01)

(52) U.S. Cl.
CPC ...... *A61N 1/0551* (2013.01); *A61B 17/00234* (2013.01); *A61B 2017/00296* (2013.01); *A61B 2017/00336* (2013.01)

(58) Field of Classification Search
CPC .......... A61B 17/00234; A61B 17/3468; A61B 2017/00296; A61B 2017/00336
See application file for complete search history.

(56) References Cited

U.S. PATENT DOCUMENTS

| | | | |
|---|---|---|---|
| 5,807,339 A | * | 9/1998 | Bostrom ........... A61M 25/0041 604/524 |
| 6,582,441 B1 | | 6/2003 | He et al. |
| 2006/0058575 A1 | | 3/2006 | Zaddem et al. |
| 2017/0266415 A1 | * | 9/2017 | Lampropoulos ....... A61N 1/056 |

FOREIGN PATENT DOCUMENTS

EP                2767306 A2     8/2014

\* cited by examiner

*Primary Examiner* — Mohamed G Gabr
(74) *Attorney, Agent, or Firm* — Bachman & LaPointe, P.C.

(57) ABSTRACT

The invention relates to a surgical application tool (18) for implanting an electrode wire on nerves in an inner area of a pelvis of a human body, the surgical application tool (18) including a mandrel (16) having an engagement tip (19) and a shaft section (02) and including a sleeve (01) which is configured to insert and guide the electrode wire through a sleeve interior (08) when the mandrel (16) is removed, the sleeve (01) extending at least along the shaft section (02) and being detachable from the mandrel (16), a handle (20) being provided on the mandrel (16) and/or the sleeve (01) for the extracorporeal handling of the application tool (18), and the handle (20) being configured to manually rotate and/or pivot the mandrel (16) and/or the sleeve (01) when it is inserted into the body. The shaft section (02) of the mandrel (16) and/or the sleeve (01) have/has at least one S-shaped segment (03) having two consecutive arc sections (05, 06), the outer arc section (06) of the S-shaped segment (03) at least partially enclosing the nerve.

17 Claims, 3 Drawing Sheets

SURGICAL APPLICATION TOOL FOR IMPLANTATION OF AN ELECTRODE WIRE

BACKGROUND OF THE INVENTION

The invention relates to a surgical application tool for implanting an electrode wire.

Methods and tools for implanting electrodes into the human body are generally known from the state of the art. In this context, implanting electrode wires, i.e., elongated, wire-shaped conductors on or in close proximity to a nerve in the human body by means of a contact surface attached to the end of the electrode wires is in particular assumed to be known. Said electrode wires are used for the signal transmission from a signal generation source to the contact surface attached to the nerve in order to be able to stimulate a nerve or a nerve ending in this manner.

In a known laparoscopic surgical technology, electrode wires can be implanted in an inner area of a pelvis or in the pelvic floor of a patient in a particularly effective manner therapeutically speaking in order to supply the stimulation signals to the pelvic nerves, in particular the nerve endings or nerve roots, in a stimulating manner.

The use of an endoscope is known for implement this technology, a working channel provided on the endoscope conductor being used as a shaft to implant the provided electrode wire by means of the endoscope under visual control. However, this surgical method is extremely complicated with regard to the handling and implementation. In view of the considerable requirements with respect to the surgical knowledge or surgical skills of the person performing the surgery, this surgical method has proven difficult to put into practice.

A generic application tool for implanting an electrode wire is known from EP 2 767 306 B1. This application tool provides a mandrel and a sleeve which is detachable from the mandrel. As a first step, the mandrel and the sleeve are jointly guided through the tissue in the inner area of the pelvis until the distal end of the application tool is placed on the corresponding nerve or nerve ending. The mandrel is then removed from the sleeve and the electrode wire is inserted into the body through the open sleeve interior. As soon as the distal end of the electrode wire exits the open end of the sleeve, the contact surface provided there can easily be contacted on the nerve or on the nerve ending.

In the area of the shaft section, the known application tool has a segment which is curved in the shape of an arc and which is adapted to the curvature of the pelvis. This geometry of the application tool has proven to be unsuitable for carrying out the implantation of electrode wires on specific nerves. In particular, the known application tool is not suitable for the implantation of an electrode wire on the sciatic nerve.

SUMMARY OF THE INVENTION

Therefore, the object of the present invention is to propose a new surgical application tool which is particularly suitable for the implantation of an electrode wire on the sciatic nerve.

Said object is attained by an application tool according to the teachings set forth herein.

Advantageous embodiments of the invention are also disclosed herein and in the subject matter of the dependent claims.

The application tool according to the invention is characterized in that the shaft section of the mandrel and/or the sleeve has at least one S-shaped segment having two consecutive arc sections. The outer arc section of the S-shaped segment is provided to at least partially enclose the nerve, in particular the sciatic nerve, on which the electrode wire is to be implanted. The S-shaped design of the shaft section in particular allows a placement of the contact surface of the electrode wire on the side of the nerve, in particular of the sciatic nerve, which faces away from the surgeon. Enclosing the nerve by means of the outer arc section allows a placement of the contact surface on the back of the nerve or of the nerve ending which faces away from the surgeon. The contact surface of the electrode wire can then approach or come into contact with the nerve surface by suitable manipulation movements and can then be attached by means of suitable methods.

In principle, the two arc sections can have any geometric design. It is especially advantageous if the outer arc section—at the distal end of which the electrode wire exits and is to be placed on the nerve or on the nerve ending—has a smaller bend radius than the inner arc section.

The outer arc section preferably extends to the distal end of the sleeve. At the distal end of the sleeve, the outer arc section particularly preferably has a linear end section which extends in particular over less than ¼, more preferably over less than ⅕, more preferably over less than ⅙, of the length of the arc section. The linear end section can preferably enclose an angle of 50° to 55° measured in relation to the stretched longitudinal axis of the sleeve. Advantageously, this allows a precise guiding and use of the applicator tool.

The large radius of the inner arc section allows a suitable guiding of the application tool through the tissue until the engagement tip of the mandrel is placed at the appropriate point of the nerve. The smaller bend radius of the outer arc section then allows the nerve to be accurately enclosed in order to place the contact surface of the electrode wire exactly on the nerve surface.

Furthermore, it is particularly advantageous for the outer arc section of the S-shaped segment to be shorter than the inner arc section of the S-shaped segment. This realizes a simple guiding of application tool through the surgical area and simultaneously allows the nerve to be enclosed precisely by means of the outer arc section.

To be able to easily place the outer arc section in such a manner that the outer arc section encloses the circumference of the corresponding nerve, the outer arc section advantageously encloses the nerve at a wrap angle of less than 180 degrees.

Furthermore, it is particularly advantageous for the outer arc section of the S-shaped segment to enclose the nerve in a hook-like manner. With respect to the manipulation of the S-shaped segment, it is also advantageous if an extension segment is provided between the S-shaped segment and the handle of the application tool.

Furthermore, a distance of the distal end of the sleeve from a stretched longitudinal axis of the sleeve is preferably reached by means of the two arc sections, the distance being between 65% and 75% of the maximal distance from a stretched longitudinal axis of the sleeve. Preferably, the maximal distance from a stretched longitudinal axis of the sleeve is reached approximately in the center of the outer arc section. An appropriate balance between direct and indirect transmission, on the one hand, and advantageous use of leverage and torques, on the other hand, can thus be exploited.

Preferably, the extension segment is to be realized in a linear manner without a separate bend radius, the extension segment thus extending linearly between the S-shaped segment and the handle.

In principle, the extension segment can have any length. For most surgical procedures, it is advantageous if the extension segment and the inner arc section of the S-shaped segment have essentially the same length.

To be able to easily handle the sleeve even after removal of the mandrel and in particular to be able to exactly place the distal open end of the sleeve at the desired point of a nerve, it is particularly advantageous for a handle element to be attached to the extracorporeal end of the sleeve. This handle element preferably has a recess through which the electrode wire can be inserted into the sleeve interior when the mandrel is removed.

If one handle element is provided on both the sleeve and the mandrel, the two handle elements should form a shared handle which can be separated.

With respect to the handling of the application tool, it is also particularly advantageous if the handle is realized in the form of a knob.

In principle, any material can be used for the mandrel of the application tool. The material should preferably be plastically or elastically deformable.

Preferably, the sleeve of the application tool is to be made of a rigid material, in particular metal or plastic.

BRIEF DESCRIPTION OF THE DRAWINGS

An embodiment of the application tool according to the invention is schematically illustrated in the drawings and is described in an exemplary manner hereinafter.

In the drawings.

DETAILED DESCRIPTION

Figure 1:
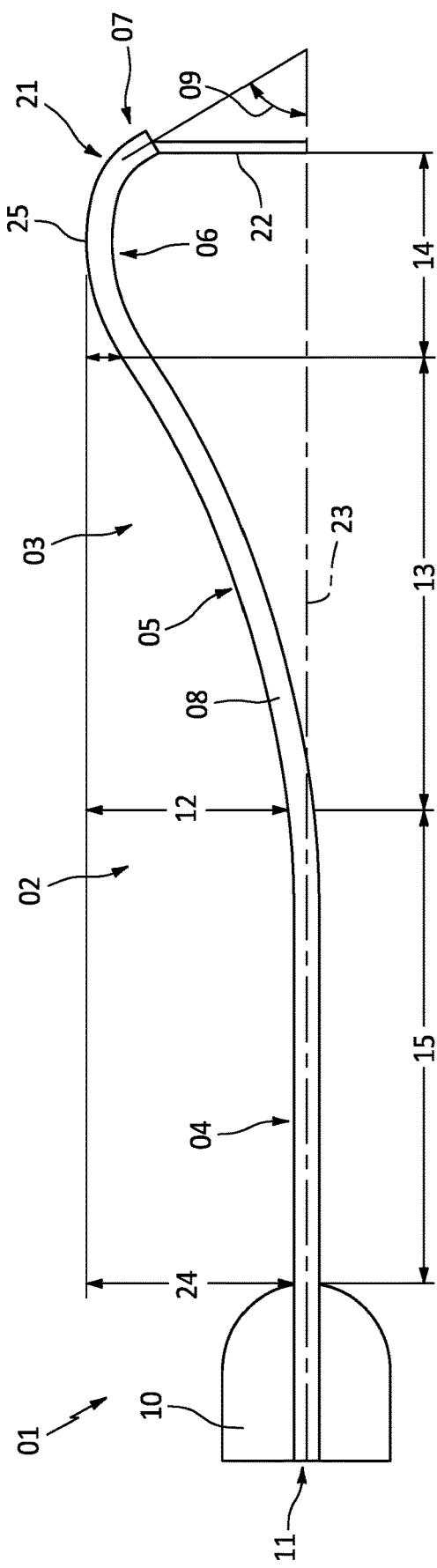
FIG. 1 shows a longitudinal view of the sleeve of the surgical application tool in the bending plane of the S-shaped segment.

FIG. 1 shows a longitudinal view of sleeve 01 of the application tool along the bending plane of sleeve 01. Sleeve 01 which can be made from a thin metal tube, for example, comprises an S-shaped segment 03 and an extension segment 04. S-shaped segment 03 is composed of an inner arc section 05 and an adjacent outer arc section 06. The outer end of outer arc section 06 is distal end 07 of sleeve 01. When the electrode wire is implanted, the electrode wire is pushed through sleeve interior 08 and exits at distal end 07. Due to the S-shaped shape of segment 03, outer arc section 06 can enclose the corresponding nerve in the inner area of the pelvis, in particular the sciatic nerve, in a hook-like manner, such that a contact surface at the end of the electrode wire exiting at distal end 07 can thus be placed on the surface of the nerve, in particular of the sciatic nerve. Because of the correspondingly larger bend radius of inner arc section 05, distal end 07 can easily be manipulated and placed by pushing the application tool forward. Hence, outer arc section 06 has a smaller bend radius than inner arc section 05.

Outer arc section 06 encloses the nerve at a wrap angle of less than 180 degrees, so that distal end 07 can easily be placed on the back of the nerve. To this end, angle 09 is chosen in the range between 50 degrees and 55 degrees, measured in relation to the stretched longitudinal axis of sleeve 01.

Extension segment 04 extends linearly between S-shaped segment 03 and a handle element 10 by means of which sleeve 01 can manually be rotated or pivoted. Handle element 10 has a recess 11 through which the electrode wire to be implanted can be inserted into sleeve interior 08 and can be pushed through to distal end 07. S-shaped segment 03 has a width 12 of approximately 7 cm. The length of S-shaped segment 03 results from length 13 of inner arc section 05, which is approximately 11 cm, and length 14 of outer arc section 06, which is approximately 3 cm. Length 15 of extension segment 04 corresponds approximately to length 13 of inner arc section 05 and is therefore also approximately 11 cm.

Outer arc section 06 extends to distal end 07 of the sleeve. Additionally, outer arc section 06 has a linear end section 21 at distal end 07 of the sleeve, said end section 21 preferably extending over more than ⅕ of the length of arc section 06.

Furthermore, a distance 22 of distal end 07 of sleeve 01 from a stretched longitudinal axis 23 of sleeve 01 is preferably reached by the two arc sections 05, 06, said distance 22 being between approximately 70% of maximal distance 24 from a stretched longitudinal axis 23 of sleeve 01. The example of FIG. 1 also shows that maximal distance 24 from a stretched longitudinal axis 23 of sleeve 01 is reached approximately in center 25 of the length of outer arc section 06.

Figure 2:
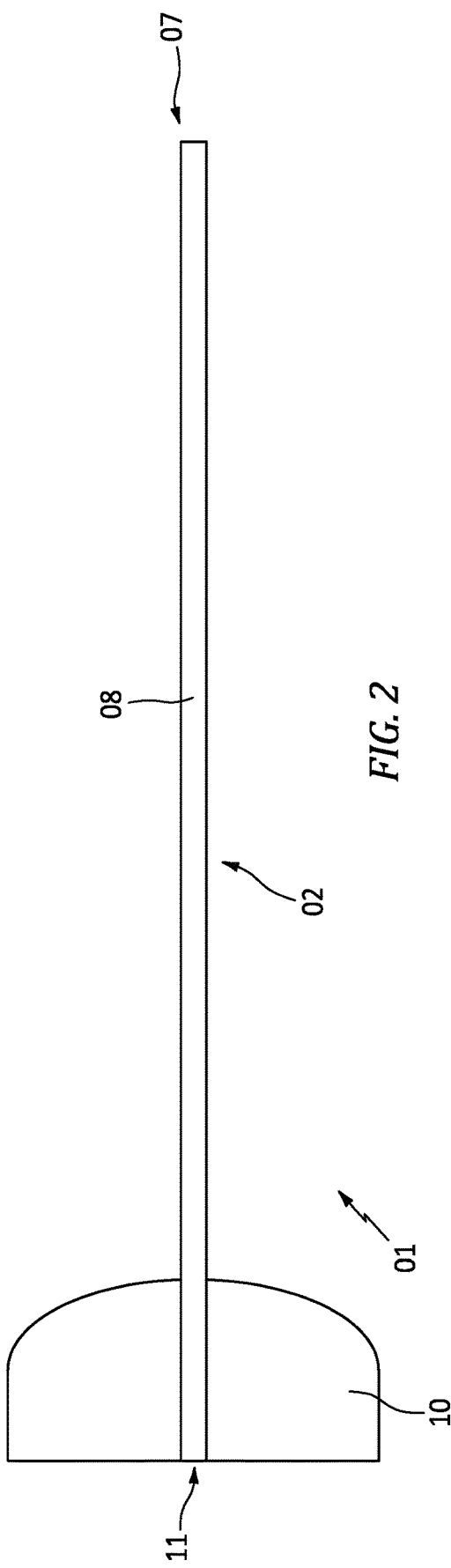
FIG. 2 shows the sleeve according to FIG. 1 in a drawing plane rotated by 90 degrees.

FIG. 2 shows sleeve 01 in a drawing plane rotated by 90 degrees. It shows that sleeve 01 has corresponding bend radii for forming S-shaped segment 03 in one plane only.

Figure 3:
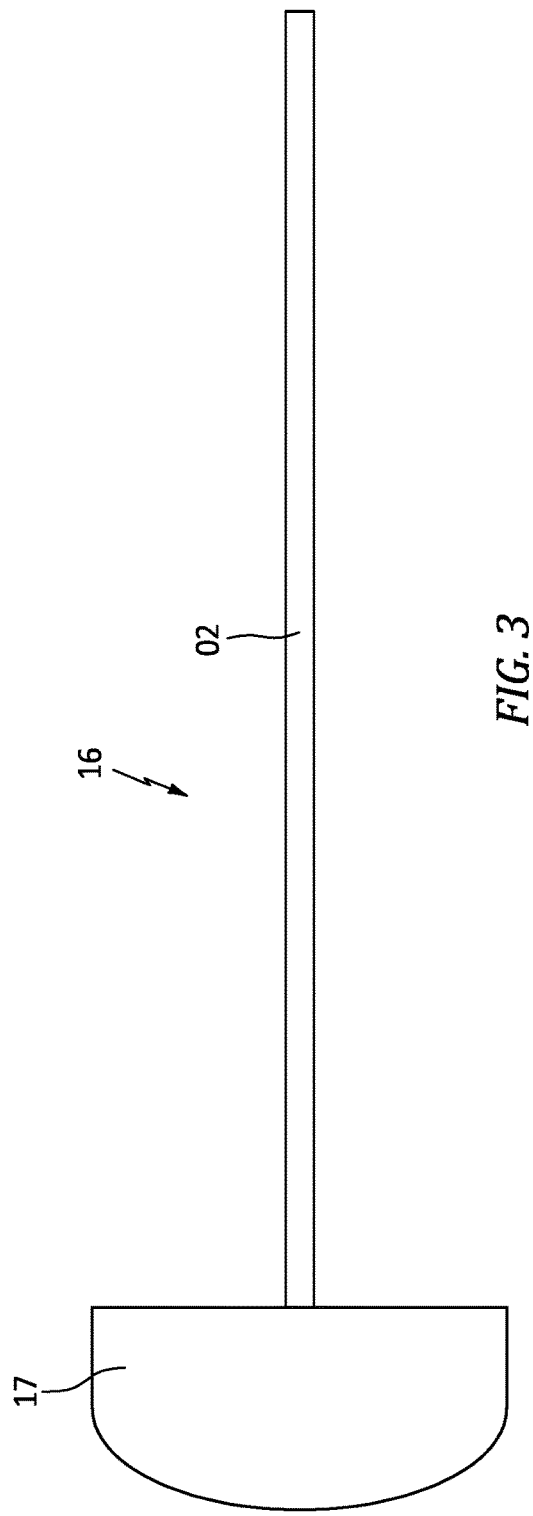
FIG. 3 shows a lateral view of the mandrel of the surgical application tool.

FIG. 3 shows mandrel 16 of the application tool, said mandrel 16 having a shaft section 02 which can be pushed through sleeve interior 08 of sleeve 01. Shaft section 02 of mandrel 16 can preferably be made from a metal wire which is simply removed after inserting sleeve 01 into the inner area of the pelvis. A handle element 17 is attached to the extracorporeal end of mandrel 16 in order to be able to manually rotate or pivot mandrel 16.

Figure 4:
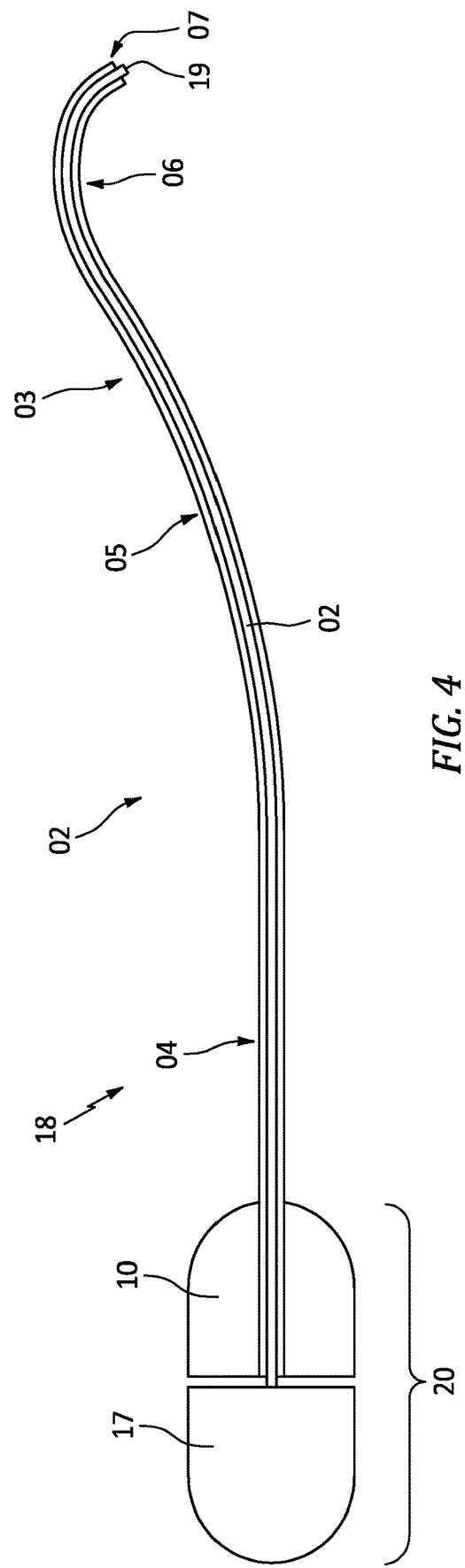
FIG. 4 shows a longitudinal view of the application tool composed of the sleeve according to FIG. 1 and the mandrel according to FIG. 3.

FIG. 4 shows application tool 18 in the assembled state. Mandrel 16 is pushed through sleeve interior 08 of sleeve 01, engagement tip 19 of mandrel 16 thus slightly protruding distal end 07 of sleeve 01. The two handle elements 10 and 17 form a shared handle 20 for manipulating application tool 18. When mandrel 16 is removed from sleeve 01, handle 20 can be separated into the two handle elements 10 and 17.

Figure 5:
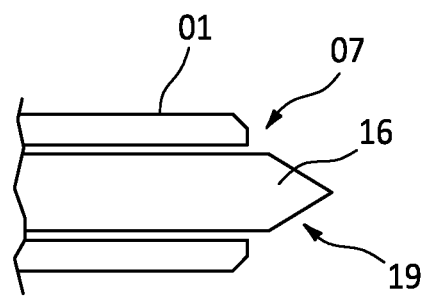
FIG. 5 shows an enlarged view of the distal end of the application tool according to FIG. 4.

FIG. 5 shows an enlarged cross section of distal end 07 of sleeve 01 which has pushed-through engagement tip 19 of mandrel 16. It shows that a complete closure of sleeve interior 08 is achieved by the insertion of mandrel 16 into sleeve interior 08; therefore, no tissue material can enter sleeve interior 08. Hence, the pushing of the electrode wire through the sleeve interior is also not hampered by tissue remnants. The tip of engagement tip is preferably not to be sharp, instead it is to be at least slightly rounded.

FIG. 5 shows an enlarged cross section of distal end 07 of sleeve 01 which has pushed-through engagement tip 19 of mandrel 16.

Figure 6:
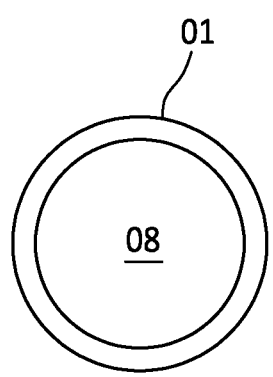
FIG. 6 shows a cross section of the sleeve of the application tool according to FIG. 1.

FIG. 6 shows a cross section of sleeve 01. Sleeve interior 08 has a diameter of approximately 3 mm; therefore, an electrode wire can easily be pushed through sleeve interior 08 after removal of mandrel 16.

REFERENCE SIGNS 01 sleeve
02 shaft section
03 S-shaped segment
04 extension segment
05 inner arc section
06 outer arc section
07 distal end
08 sleeve interior
09 intermediate angle
10 handle element
11 recess
12 width
13 length
14 length
15 length
16 mandrel
17 handle element
18 application tool
19 engagement tip
20 handle
21 end section
22 distance at distal end 07
23 stretched longitudinal axis
24 maximal distance
25 center of outer arc section 06

The invention claimed is:

1. A surgical application tool (18) for implanting an electrode wire on nerves in an inner area of a pelvis of a human body, the surgical application tool (18) comprising a mandrel (16) having an engagement tip (19) and a shaft section (02) and comprising a sleeve (01) made of a rigid material which is configured to insert and guide the electrode wire through a sleeve interior (08) when the mandrel (16) is removed, said sleeve (01) extending at least along the shaft section (02) and being detachable from the mandrel (16), a handle (20) being provided on the mandrel (16) and/or the sleeve (01) for the extracorporeal handling of the application tool (18), and the handle (20) being configured to manually rotate and/or pivot the mandrel (16) and/or the sleeve (01) when it is inserted into the body,
wherein
the shaft section (02) of the mandrel (16) and/or the sleeve (01) have/has at least one S-shaped segment (03) having two consecutive arc sections (05, 06), an outer arc section (06) of the S-shaped segment (03) being configured to at least partially enclose the nerve, and
wherein
when the mandrel (16) is inserted through the sleeve (01), a complete closure of an interior of the sleeve is achieved.

2. The surgical application tool according to claim 1, wherein the outer arc section (06) has a smaller bend radius than the inner arc section (05).

3. The surgical application tool according to claim 1, wherein in that the outer arc section (06) of the S-shaped segment (03) is shorter than the inner arc section (05) of the S-shaped segment (03).

4. The surgical application tool according to claim 1, wherein the outer arc section (06) of the S-shaped segment (03) can enclose the nerve at a wrap angle of less than 180 degrees.

5. The surgical application tool according to claim 1, wherein the outer arc section (06) of the S-shaped segment (03) can enclose the nerve in a hook-like manner.

6. The surgical application tool according to claim 1, wherein an extension segment (04) is provided between the S-shaped segment (03) and the handle (20).

7. The surgical application tool according to claim 6, wherein the extension segment (04) extends linearly between the S-shaped segment (03) and the handle (20).

8. The surgical application tool according to claim 6, wherein the extension segment (04) and the inner arc section (05) have essentially the same length.

9. The surgical application tool according to claim 1, wherein a handle element (10) is attached to the extracorporeal end of the sleeve (01), the handle element (10) having a recess (11), and the electrode wire being insertable through the recess (11) into the sleeve interior (08) when the mandrel (16) is removed.

10. The surgical application tool according to claim 1, wherein the handle (20) is separable into two handle elements (11, 17), the first handle element (11) being attached to the extracorporeal end of the sleeve (01), and the second handle element (17) being attached to the extracorporeal end of the mandrel (16).

11. The surgical application tool according to claim 1, wherein the handle (20) is realized in the form of a knob.

12. The surgical application tool according to claim 1, wherein the mandrel (16) is made of a plastically or elastically deformable material and is more elastic than the sleeve.

13. The surgical application tool according to claim 1, wherein the rigid material is a metal or plastic.

14. The surgical application tool according to claim 1, wherein the sleeve (1) comprises a metal tube.

15. The surgical application tool according to claim 1, wherein the sleeve (01) extends from a proximal handle end to a distal end having an opening for the engagement tip (19) of the mandrel (16), and wherein the sleeve (01) is sufficiently rigid from the proximal handle end to the distal end that the sleeve (01) will not flex or bend under forces encountered during use in positioning the distal end at a pelvic nerve.

16. The surgical application tool according to claim 1, wherein a lateral distance of a distal end of the sleeve (01) from a longitudinal axis of the sleeve is reached by means of the two consecutive arc sections, the distance being between 65% and 75% of a maximal lateral distance from the longitudinal axis of the sleeve.

17. The surgical application tool according to claim 16, wherein the maximal lateral distance from the longitudinal axis of the sleeve is reached in a center of the outer arc section.

* * * * *